United States Patent [19]

Stoutamire et al.

[11] Patent Number: 4,594,196

[45] Date of Patent: Jun. 10, 1986

[54] PREPARATION OF OPTICALLY ACTIVE ALPHA-HYDROXYNITRILES

[75] Inventors: Donald W. Stoutamire, Modesto, Calif.; Walter Dong, Houston, Tex.

[73] Assignee: Shell Oil Company, Houston, Tex.

[21] Appl. No.: 551,548

[22] Filed: Nov. 14, 1983

Related U.S. Application Data

[63] Continuation-in-part of Ser. No. 443,763, Nov. 22, 1982, abandoned.

[51] Int. Cl.$^4$ .......................................... C07C 121/66
[52] U.S. Cl. .................................. 588/351; 546/300; 558/405; 558/410; 558/388
[58] Field of Search .................. 260/465 F, 465 G; 546/300

[56] References Cited

PUBLICATIONS

Oku, J. et al., *J.C.S. Chem. Comm.*, pp. 229–230 (1981).
Oku, J. et al., *Makromol. Chem.*, 183, pp. 579–586 (1982).
Oku, J., *Kagaku Kogyo*, 32 (11), pp. 1134–1136 (62–64), Nov. 1981 and translation.

*Primary Examiner*—Alan L. Rotman

[57] ABSTRACT

Preparation of certain optically-active alpha-hydroxynitriles or a mixture enriched therein comprises treating an aldehyde with hydrogen cyanide in a substantially water-immiscible, aprotic solvent in the presence of a cyclo(D-phenylalanyl-D-histidine) as a catalyst.

16 Claims, No Drawings

PREPARATION OF OPTICALLY ACTIVE ALPHA-HYDROXYNITRILES

CROSS-REFERENCE TO RELATED APPLICATIONS

This application is a continuation-in-part of U.S. Ser. No. 443,763, filed Nov. 22, 1982, now abandoned.

BACKGROUND OF THE INVENTION

1. Field of the Invention

The present invention is directed to a process for the preparation of optically-active alpha-hydroxynitriles.

2. Description of the Prior Art

Optically-active alpha-hydroxy benzonitriles are known in the art and are of interest, per se, and as intermediates, e.g. to esters. In aldehyde derived pyrethroid esters, those having an alpha-S alpha-hydroxynitrile moiety coupled with the appropriate pyrethroid acid usually have the highest pesticidal activity. However, such alpha-S alpha-hydroxynitriles have not been easily obtained in the past because they were usually prepared by resolution.

SUMMARY OF THE INVENTION

The present invention is directed to a process for the preparation of optically-active alpha-hydroxynitriles of formula I below

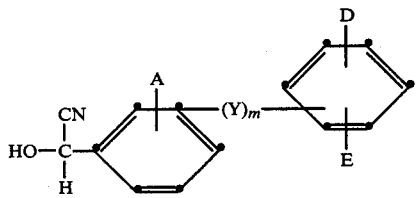

wherein m is 0 or 1; Y is O, $CH_2$, or C(O); A, D and E each independently is a hydrogen atom, a halogen atom having an atomic number of from 9 to 35, inclusive, or an alkyl or alkoxy group containing 1 to 6 carbon atoms, each optionally substituted by one or more halogen atoms having an atomic number of from 9 to 35, inclusive, or a mixture enriched therein which comprises treating the corresponding aldehyde with a source of hydrogen cyanide in a substantially water-immiscible, aprotic solvent and in the presence of a cyclo-(D-phenylalanyl-D-histidine) dipeptide as a catalyst. These products of formula I are optically-active, optionally-substituted S-alpha-cyanobenzyl alcohols.

A substantially water-immiscible, aprotic solvent for use in this invention is defined as an aprotic solvent in which the solubility in water is not more than 5%v, at the reaction temperature (and does not interfere with the reaction). For example, the solvent is a hydrocarbon, or ether solvent including acyclic, alicyclic or aromatic materials. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Useful ethers include diethyl ether, diisopropyl ether, methyl-t-butyl ether and the like. Preferably, the solvent has a boiling point below about 150° C. Preferably, the solvent is an aromatic hydrocarbon, especially toluene, diisopropyl ether or diethyl ether or mixtures thereof (e.g. 25/75 of diethyl ether/toluene). Toluene gives especially high enantiomeric excess when the substrate is 3-phenoxybenzaldehyde. Advantages of diethyl ether are the rate of reaction and that the catalyst is not soluble and can be recovered as a solid at the end of the reaction.

The process of the present invention is suitably applied to compounds of formula I wherein m is 1 and Y is O. These products are optically-active optionally-substituted S-alpha-cyano-3-phenoxybenzyl alcohols. Preferably, A, D or E each independently is a hydrogen atom, a fluorine atom, a chlorine atom, a methyl group, a trifluoromethyl group or methoxy group. Preferably, one of D and E is a hydrogen atom. An especially preferred embodiment of the alpha-hydroxynitriles are those of the formula above in which D is a hydrogen atom and A and E each independently is a fluorine atom or a hydrogen atom, and, preferably, when either A or E is fluorine, each is located at the 4-position of the ring relative to the benzyl carbon when A or relative to the Y=O bearing carbon atom when E. Especially suitable alcohols are when A is a fluorine atom at the 4-position or a hydrogen atom and E is a hydrogen atom.

Non-limiting examples of alpha-hydroxynitriles of the above formula I include S-alpha-cyano-3-phenoxybenzyl alcohol, S-alpha-cyano-4-fluoro-3-phenoxybenzyl alcohol, S-alpha-cyano-3-(4-fluorophenoxy)benzyl alcohol, and the like.

The amount of catalyst can vary. For example, it can be used in the range of from about 0.1 to about 10 mole percent based upon the weight of the aldehyde present, especially about 1.0 to about 7.5 mole percent. The catalyst is preferably well dispersed in the reaction mixture.

When the catalyst is prepared by conventional methods in the presence of water, and as a solid, it can also contain solvent (e.g. water) of crystallization. The optically-active cyclo(D-phenylalanyl-D-histidine) catalyst of the invention thus includes the presence or absence of solvent (e.g. water) of crystallization. The presence of a small amount of water in the reaction system is acceptable and, at least in the case of toluene as a solvent, appears to enhance the reaction.

Preferably, an aldehyde reactant has the formula II

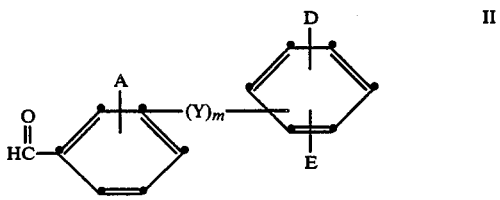

wherein m, A, D, E and Y have the same meanings as given in the formula I above.

Examples of suitable aldehydes of the formula above include 3-phenoxybenzaldehyde, 4-fluoro-3-phenoxybenzaldehyde, and the like.

The source of cyanide ions is hydrogen cyanide or an agent which generates hydrogen cyanide such as a simple alpha-hydroxynitrile such as acetone cyanohydrin, under the reaction conditions. Hydrogen cyanide itself is preferred. The molar ratio of hydrogen cyanide to aldehyde is from about 1.0 to about 3.0 moles per mole of aldehyde and, preferably, from about 1.1 to about 2.0.

The preferred embodiment of the present invention is directed to a catalyst for cyanohydrination of aldehydes, comprising a solid cyclo(D-phenylalanyl-D-histidine) having a substantially non-crystalline component as claimed in co-pending U.S. Ser. No. 535,500, filed Sept. 26, 1983, and also described below.

In other words, the catalyst has a component having a substantially amorphous or non-crystalline structure. While the precise form of this cyclo(D-phenylalanyl-D-histidine) dipeptide is not known, it appears that in the activated (amorphous or non-crystalline) form, a number of the available —NH groups in the dipeptide are free of intermolecular hydrogen bonding to the available —C=O groups of the dipeptide crystal lattice as compared to the less active (crystalline component) form. This is believed to involve the formation of a less bonded linear or planar (or sheet) form of peptide structure as opposed to the highly bonded ribbon (or chain) form of peptide structure because of the increase in the number of —NH groups free of intermolecular hydrogen bonding to available —C=O groups in the dipeptide lattice. Such being the case, the degree of amorphousness or non-crystallinity is most readily determined by X-ray diffraction.

The wide-angle X-ray scattering (WAXS) measurements were carried out in reflection by means of a Philips APD3600/02 automated X-ray diffractometer. The samples were scanned at 20° C. in air from 5.0° to 60.0° $2\theta$ at 0.02 degree increments, and 0.6 second time increments with Cu $K\alpha$ radiation (40 KV, 35ma).

The percent crystallinity was determined by a modified Hermans and Weidinger method (P. H. Hermans and A. Weidinger, *Makromol. Chem.*, 50, 98 (1961)). The diffuse background scattering below the main peaks was constructed assuming a linear baseline between $5° \leq 2° \leq 60°$ and approximating the amorphous scattering with a smooth curve. The X-ray crystallinity, $W_c$, was calculated from the integrated crystalline and amorphous intensities $F_c$ and $F_a$ by the equation $W_c = F_c/(F_c + F_a)$. The various definitions can be found in the text H. P. Klug and L. E. Alexander, *X-Ray Diffraction Procedures for Polycrystalline and Amorphous Materials*, Wiley-Interscience, New York, (1974).

As used herein the terms "amorphous" or "non-crystalline" define active catalyst materials which have about 20% or more of an amorphous or non-crystalline component as determined by the area of the X-ray diffraction spectra obtained by the method described above. Preferably, the "amorphous" or "non-crystalline" component of the materials as defined by the X-ray diffraction spectra is about 45% to about 65% or higher. Preferably, the "amorphous" or "non-crystalline" component is about 65% or higher.

The catalysts are also analyzable by photomicrographs in which inefficient catalysts consist of agglomerates of fine crystallites. Crystallites are not evident in photomicrographs of active catalysts, which when, for example, are spray-dried, take the form of hollow-appearing spheres.

Alternative methods are available to define the terms amorphous and non-crystalline by infrared or nuclear magnetic resonance spectral studies or by swelling of the material, e.g. in contact with the reactants of the cyanohydrination process.

In a preferred method the dipeptide is prepared by the route described below in which HIS means histidine and PHE means phenylalanine.

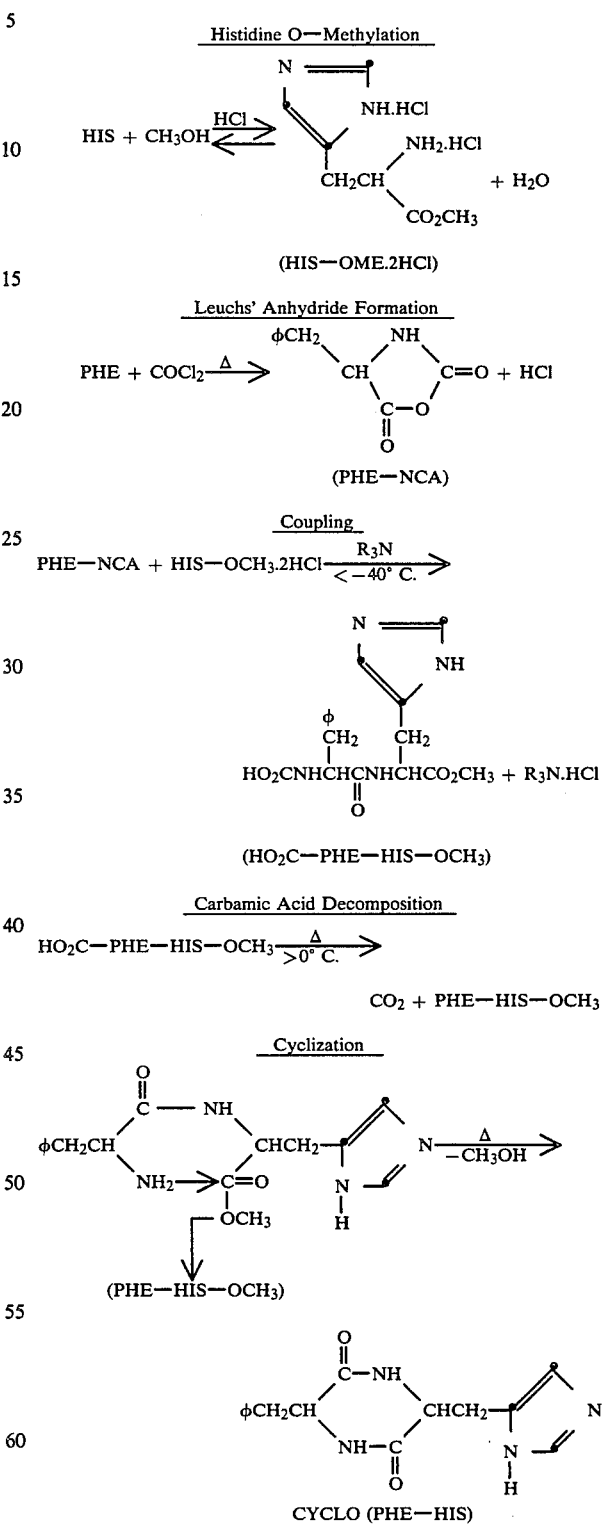

When the catalyst is prepared by conventional methods in the presence of water, and as a solid, it can also contain solvent (e.g. water) of crystallization. The optically-active, cyclo(D-phenylalanyl-D-histidine) dipeptide catalyst of the invention thus includes the presence or absence of solvent (e.g. water) of crystallization.

The solid catalyst can be recovered by extraction with acid followed by neutralization with a base or preferably by treating with (dissolving in) a solvent, for example a hydroxylic solvent, including lower alkanols of 1 to 10 carbon atoms such as isopropanol or preferably methanol (preferably with heating, e.g. to reflux or quick flash), and reprecipitating (preferably below ambient temperature) which produces a less crystalline (or more amorphous) catalyst structure.

While it is preferred to directly prepare the catalyst of the present invention having the non-crystalline component, it is also within the scope of this invention to prepare a substantially crystalline catalyst and to subsequently activate the catalyst by converting at least part of the crystalline material to an amorphous form. Thus, the present invention is directed to both a method of direclty preparing an active cyclo(D-phenylalanyl-D-histidine) dipeptide catalyst and to a method of activating a crystalline catalyst of this type, which methods both involve reducing or preventing the formation of a substantially crystalline form thereof. In the case of activation of a crystalline catalyst, the crystalline form is first broken down and then prevented at least in part from reforming.

It is believed that the breakdown of or the prevention of the formation of a number of intermolecular bonds between the amino N—H and the carboxyl C═O groups in the crystal lattice makes the catalyst have an amorphous or non-crystalline form. In any event, an ordered deposition of crystals of the catalyst is discouraged or reduced.

Any means which will accomplish this reduction or prevention either during the catalyst preparation or an after treatment are within the scope of the invention. Among the illustrative examples of methods which reduce or prevent the formation of a highly crystalline form or highly ordered arrangement are (a) very rapid evaporation of a solution of the catalyst, in the presence or absence of impurities or crystallinity inhibitors; (b) rapid precipitation of the catalyst from solution by dilution in a poor solvent; (c) freeze drying of a solution of the catalyst; (d) rapid cooling of the melted catalyst in the presence or absence of impurities or crystallinity inhibitors; (e) use of crystallinity inhibitors during solidification; and the like.

The unactivated dipeptide catalyst, when recovered at the end of a conventional synthesis process, is often almost completely inactive in the cyanohydrination reaction, apparently because it has become highly crystalline as can be determined by X-ray diffraction. Activation, as used herein, appears to involve converting at least part of the normally crystalline material into an amorphous form such that the dipeptide is swelled by the reaction mixture and the chiral base function of the catalyst is made accessible to the reactants. In order to produce high chirality in the cyanohydrination product, it appears that the catalyst should preferably be essentially insoluble in the cyanohydrination solvent.

The first step in converting what is or what normally would be a crystalline material to an amorphous form is to break down (or prevent) formation of the intermolecular bonds in the crystal lattice. The breakdown readily occurs when the material is melted or dissolved in a solvent. Once this has been accomplished, a method is used that will allow the separation of the dissolved material from the solvent at a rate such that normal crystallization cannot occur. There are a number of ways in which this might be effected: (a) rapid evaporation of the solvent, e.g. as in a spray dryer; (b) rapid precipitation of the material by pouring a solution of it into a large volume of a different solvent that is miscible with the original solvent but does not dissolve, to a large extent, the material to be precipitated; (c) rapid freezing of a solution followed by sublimation of the solvent (freeze drying); (d) rapid cooling of the melted catalyst; and (e) use of inhibitors alone or with any of the above methods (a)–(d). Preferably, the method used is a) rapid evaporation of the solvent and, especially, by means of spray drying.

Because of the polar nature and high melting point ($\sim$250° C.) of cyclo(D-phenylalanyl-D-histidine), the choice of solvents that will dissolve it to any appreciable extent is very limited. Potential solvents suitable and unsuitable that have been tested are listed in Table 1 in order of decreasing effectiveness, and the use of these will be discussed below in relation to the method of catalyst activation via recovery techniques or specific subsequent activation treatment.

TABLE 1

| SOLVENTS TESTED FOR SOLUBILITY OF CYCLO(D-PHENYLALANYL-D-HISTIDINE) | | |
|---|---|---|
| Solvent | B.P./°C. | Solvency |
| Dimethyl Sulfoxide | 189 | Good (5–10% w) |
| Acetic Acid | 118 | Good |
| Formamide | 210 | $\geq$2.3% at 25° C. |
| 1-Methyl-2-pyrrolidinone | 202 | $\geq$2.2% at 25° C. |
| Dimethylformamide | 153 | Fair to Good, <5% at 90° C. |
| Liquid Ammonia | −33 | $\sim$2% at −40° C. |
| N—methylformamide | 185 | $\geq$2.4% at 25° C. |
| Acetonitrile | 80 | Fair to Poor, < <5% at 70° C. |
| Methanol | 64 | 1% w Hot, 0.3% w at 25° C. |
| Water | 100 | Fair to Poor, 0.1% at 25° C. |
| Acetone | 55 | Fair to Poor, < <1% at 25° C. |
| Liquid Carbon Dioxide | −78 | Poor, <0.2% at 25° C. |
| Carbon Disulfide | 45 | Very Poor |
| Diethyl Ether | 35 | Very Poor |
| Hydrocarbons | Var | Very Poor |

The use of crystallization inhibitors is an alternative method of reducing or preventing the crystalline form of the dipeptide. Many chemicals can be used. It is useful if the crystallization inhibitor has a similar kind of structure or has one or more substituents similar in kind to those found in the dipeptide, but the inhibitor is not identical to the units of the dipeptide. In the case of this dipeptide, useful kinds of crystallization inhibitors include those materials containing a —N—H and/or —C═O group, including ureas, aldehydes and amines. Even by-product impurities of the dipeptide process containing such substituents are useful crystallization inhibitors, e.g. making an impure product can make a more active catalyst.

The reaction to prepare alpha-hydroxynitriles is suitably conducted by adding the adlehyde and solvent to the cyclo(D-phenylalanyl-D-histidine) catalyst, dispersing (mechanical grinding or agitating the mixture, e.g. by stirring), adding hydrogen cyanide and maintaining the reaction conditions for an amount of time to effect the formation of the optically-active alpha-hydroxynitrile. That is, preferably, the hydrogen cyanide is introduced concurrently with or subsequent to the solvent and/or aldehyde to increase the conversion and stereoselectivity. The presence of cyanide ions appears to have an adverse effect on the catalyst in this reaction.

In any event, competing racemization is reduced by protecting the catalyst from cyanide ions. The forming and maintaining of a well dispersed but not necessarily homogeneous-like reaction mixture are useful. Separation and recovery of the optically-active ester product are achieved by conventional techniques, including extraction and the like.

The temperature of the reaction to prepare alpha-hydroxynitriles as well as the pressure can vary. At normal pressures, the temperature is from about −10° C. to about 80° C., more or less. Preferably, ambient temperatures of about 5° C. to about 35° C. are convenient to give good yield, rate of reaction and enantiomeric excess of the desired optically-active product, the lower temperature of about 5° C. giving good results.

The alpha-hydroxynitriles and their corresponding aldehydes are generally known in the literature. The S-benzyl alcohols are of interest per se or as intermediates to esters, e.g. of the pyrethroid type, for example, S-alpha-cyano-3-phenoxybenzyl alcohol in U.S. Pat. No. 4,273,727 or those described in U.S. patent application Ser. No. 443,513, filed Nov. 22, 1982.

Another embodiment of the invention is directed to a process for the preparation of an optically-active cyanomethyl ester or a mixture enriched therein which comprises treating an alpha-chiral (optically-active) carboxylic acid halide or reactive derivative thereof, or mixture enriched therein, with an optically-active, optionally substituted alpha-hydroxynitrile(S-alpha-cyanobenzyl alcohol) or mixture enriched therein which has been prepared as described above.

This process of the invention is useful for preparing esters from any optically-active acid halides or other reactive derivatives thereof (reactive derivatives of the carboxylic acid) (which do not contain substituted groups which would react with the base, when present). For example, the acid halide can be that of an acyclic, alicyclic, aromatic or heteroaromatic acid.

The reaction is conducted in the absence of a solvent or in the presence of an organic solvent, which is suitably selected from non-hydroxylic solvents such as hydrocarbons, chlorinated hydrocarbons, ethers and the like, including those described above for the process for the preparation of the alpha-hydroxynitriles. Preferably, the solvent is an aromatic solvent, such as toluene.

The reaction with acid halide is preferably conducted in the presence of a hydrogen halide acceptor, which is suitably a tertiary amine including a trialkylamine, such as triethylamine, a pyridine, such as pyridine or 2,6-lutidine, and the like, added slowly with agitation and usually after the other reactants are well mixed.

The reaction to prepare optically-active cyanomethyl esters from the S-alcohols and alpha-chiral carboxylic acid halides or reactive derivative thereos is also suitably conducted under phase-transfer conditions in the presence of a phase-transfer catalyst, which effectively facilitates the transfer of ions or other reactive or functional chemical species across the phase interface as in heterogeneous systems. Non-limiting examples of phase-transfer catalysts include certain organic quaternary salts of Group VA elements of the Periodic Table of Elements, e.g. of nitrogen, phosphorus, arsenic, antimony and bismuth.

The preferred phase-transfer catalysts are tetra-n-butyl phosphonium chloride, tri-n-butyl n-octyl phosphonium bromide, hexadecyl tributyl phosphonium bromide, benzyl triethyl ammonium chloride, benzyl triethyl ammonium bromide, trioctyl ethyl ammonium bromide, tetraheptyl ammonium iodide, triphenyl decyl phosphonium iodide, tribenzyl decyl ammonium chloride, tetranonyl ammonium hydroxide, tricaprylyl methyl ammonium chloride and dimethyl dicoco ammonium chloride. The last two catalysts are manufactured by General Mills Company, Chemical Division, Kankakee, Ill., and are alternatively designated by the names "Aliquat 336$^{(R)}$" and "Aliquat 221$^{(R)}$", respectively.

In the preparation of the esters, the molar ratio of the starting materials can be varied widely. For example, the molar ratio of acid halide to alcohol is from about 10:1 to about 1:10, and preferably from about 5:1 to about 1:5. Howevr, it is desirable to have a molar excess of acid halide to alcohol. Therefore, a molar ratio of alcohol to acid halide is desirably from about 1:1 to about 1:5 and conveniently from about 1:1 to about 1:1.2.

In the preparation of the ester, the temperature can be varied widely. At normal pressure, for example, the temperature of reaction can be varied, for example, from about 0° C. to about 70° C., but is preferably from about 10° C. to 40° C. more or less.

Separation and recovery of the product ester are achieved by conventional methods, including crystallization and the like.

This embodiment of the process of the invention is useful for preparing esters from any acid halide, or reactive derivative thereof, which do not contain substituted groups which would react with the base. For example, the acid halide or reactive derivatives thereof are conventionally known in the art and include an acyclic, alicyclic, aromatic or heteroaromatic acids, and reactive derivatives thereof and preferably has the formula III

wherein X is a halogen atom or a reactive derivative of the halide; $R^1$ and $R^2$ each independently is an alkyl, aralkyl, alkoxy, aryloxy, alkylthio, alkylsulfonyl, arylthio, or arylsulfonyl group containing from 1 to 10 carbon atoms or a cycloalkyl group containing 3 to 7 ring carbon atoms, or when taken together with the carbon atom to which they are attached form a non-symmetrical cycloalkyl group containing 3 to 7 ring carbon atoms; $R^2$ is also an alkenyl or alkynyl containing from 2 to 10 carbon atoms; a naphthyl group; a phenyl group; a heterocyclic group containing 5 or 6 ring atoms, one of which is oxygen, sulfur or nitrogen, and the remainder are carbon atoms, or is an amino group disubstituted by acyl, alkyl containing up to 10 carbon atoms, or a phenyl group. The $R^1$ and $R^2$ groups can be optionally substituted by one or more of halogen of atomic numbers 9 to 35, an alkyl, haloalkyl or cycloalkyl group containing up to 7 carbon atoms, alkenyl or haloalkenyl group of 2 to 4, haloalkoxy or alkoxy group of 1 to 4 carbon atoms, haloalkylthio or alkylthio group of 1 to 4 carbon atoms or equivalent kinds of substituents. As reactive derivatives halides are preferred, e.g. of formula III above in which X is chlorine or bromine.

One class of acid halides are of pyrethroid acids, including those of U.S. Pat. Nos. 4,024,163, 4,062,968, 4,220,591, 3,835,176, 4,243,819, 4,316,913 and 4,199,595. Examples of such acid halides or reactive derivatives thereof include those having the formula III in which $R^1$ is isopropyl or cyclopropyl; $R^2$ is an alkyl group containing 1 to 6 carbon atoms; an alkenyl group containing 2 to 6 carbon atoms; a naphthyl group, a phenyl group or a (benzyloxycarbonyl)phenylamino group, each optionally ring-substituted by one or more of halogen, alkyl, haloalkyl, alkoxy, haloalkoxy in which the halogens are bromine, chlorine or fluorine and the alkyl groups contain 1 or 4 carbon atoms, or $R^1$ and $R^2$ together with the carbon atom to which they are attached form a cyclopropyl group of the formula

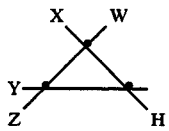

in which W, X, Y and Z each independently is a hydrogen atom, a halogen atom of atomic numbers 9 to 35 or an alkyl group containing 1 to 4 carbon atoms or Y and Z each independently is an alkyl group containing 1 to 4 carbon atoms, W is a hydrogen atom and X is pentahaloethyl, dihalovinyl, isobutenyl, perhalomethylvinyl, 2-phenyl-2-halovinyl 2-phenyl-1,2,2-trihaloethyl group or alkoxyiminomethyl or ((cycloalkyl)alkoxy)iminomethyl of 1 to 10 carbon atoms. For example, the acid halide is isopropyl(4-chlorophenyl)acetyl chloride, isopropyl(4-(difluoromethoxy)phenyl)acetyl chloride, isopropyl((4-trifluoromethyl-3-chlorophenyl)(benzyloxycarbonyl)amino)acetyl chloride, 2,2-dimethyl-3-(2,2-dichlorovinyl)cyclopropanecarbonyl chloride, 2,2-dimethyl-3-(2,2-dibromovinyl)cyclopropanecarbonyl chloride, 2,2-dimethyl-3-(1,2-dibromo-2,2-dichloroethyl)cyclopropanecarbonyl chloride, 1-(4-ethoxyphenyl)-2,2-dichlorocyclopropanecarbonyl chloride, 2,2-dimethyl-3-(2-(trifluoromethyl)-2-chlorovinyl)cyclopropanecarbonyl chloride, 2,2-dimethyl-3-((isobutoxyimino)methyl)cyclopropanecarbonyl chloride, 2,2-dimethyl-3-((neopentoxyimino)methyl)cyclopropanecarbonyl chloride, 2,2-dimethyl-3-(((cyclobutyl)methoxyimino)methyl)cyclopropanecarbonyl chloride, or chrysanthemyl chloride, and the like.

Preferably, in formula III, $R^1$ is isopropyl and $R^2$ is a phenyl group optionally substituted by halogen, an alkyl or haloalkyl group of 1 to 4 carbon atoms or an alkoxy or haloalkoxy group containing 1 to 4 carbon atoms, preferably at the para position, especially useful are 4-chlorophenyl, 4-(difluoromethoxyphenyl), 4-methylphenyl, 4-tert-butylphenyl and the like.

In one embodiment of the invention, an S-alpha-cyano-3-phenoxybenzyl alcohol or mixture enriched therein is treated with an S-alpha-isopropylphenylacetic acid chloride or an optionally-substituted chiral cyclopropanecarboxylic acid chloride to give an optically-active cyanomethyl ester or a mixture enriched therein.

The cyanomethyl esters for which the optically-active form is prepared by one or more embodiments of the process of the invention, i.e. of formula IV

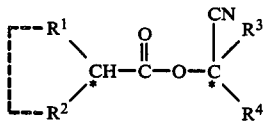

are generally known in the art, including from Francis et al., *J. Chem. Soc.*, 95, pages 1403–1409 (1909) and the like, and in the optical forms, including U.S. Pat. Nos. 4,151,195, 4,239,737, 4,328,167 and 4,133,826, and British Pat. No. 2,014,137 and the like. Any of the alpha-cyanomethyl esters prepared can be hydrolyzed to their corresponding acids by conventional hydrolysis methods known in the art. Preferably, the product optically-active ester is S-alpha-cyano-3-phenoxybenzyl S-alpha-isopropyl(p-chlorophenyl)acetate, S-alpha-cyano-3-phenoxybenzyl S-alpha-isopropyl(p-(difluoromethoxy)phenyl)acetate, S-alpha-cyano-3-phenoxybenzyl (1R,cis)-3-(2,2-dichlorovinyl)-2,2-dimethylcyclopropanecarbonoxylate, S-alpha-cyano-3-phenoxybenzyl (1R,cis)-3-(2,2-dibromovinyl)-2,2-dimethylcyclopropanecarboxylate, S-alpha-cyano-3-phenoxybenzyl (1R,cis)-3-(1,2-dibromo-2,2-dichloroethyl)-2,2-dimethylcyclopropanecarboxylate, S-alpha-cyano-3-phenoxybenzyl (1R,cis)-2,2-dimethyl-3-(neopentoxyiminomethyl)cyclopropanecarboxylate, and the like.

ILLUSTRATIVE EMBODIMENTS

The following embodiments are provided for the purpose of illustrating the invention and should not be regarded as limiting it in any way. The identity of the products was confirmed by infrared and nuclear magnetic resonance spectral analyses.

EMBODIMENT 1

N-(BENZYLOXYCARBONYL)-D-PHENYLALANINE

A 15.0 g sample of D-phenylalanine was dissolved in 45 ml of aqueous solution containing 7.26 g of 50% sodium hydroxide. This solution was stirred at 0°–10° C. as 16.3 g of benzyl chloroformate was added rapidly in portions. The resulting reaction was mildly exothermic, and shortly after addition, solids precipitated. An additional 45 ml of water and 3.63 g of 50% sodium hydroxide were added, causing most of the solids to redissolve. The reaction mixture was stirred for 20 minutes and then acidified with 6 N hydrochloric acid. The resulting solids were filtered, washed with water and then with hexane, and dried by suction and then under vacuum to give 47 g of white solids. These solids dissolved in ether were washed twice with 1 N hydrochloric acid and then with water, dried over $MgSO_4$ and stripped to 35° C. at 2.5 mm Hg to give 27.7 g of the desired product as a colorless oil.

EMBODIMENT 2

N-(BENZYLOXYCARBONYL)-D-PHENYLALANINE, P-NITROPHENYL ESTER

A 300 ml three-neck flask with stirrer and dropping funnel was charged under a nitrogen atmosphere with 27 g of the acid of Embodiment 1 above in 135 ml of pyridine, followed by 13.2 g of p-nitrophenol. The resulting solution was cooled to 0° to 10° C. as 14.6 g of phosphorus oxychloride was added. The resulting mixture was warmed to 25° C., stirred for 15 minutes, then poured into 300 ml of ice water. Filtration of the resulting solid, followed by washing with water and drying by suction, gave 33 g of product. This was crystallized from 340 ml of hot ethyl alcohol with chilling to −5° C. The product was filtered, washed with chilled ethyl alcohol, then with hexane, and sucked dry to give 28.7 g of the desired product, m.p. 122.5°–124.5° C., $[\alpha]_D^{23}$ 24.7 (c 2.0, dimethylformamide).

EMBODIMENT 3

N-(BENZYLOXYCARBONYL)-D-PHENYLALA-NYL-D-HISTIDINE METHYL ESTER

To a stirred solution of 5.0 g of D-histidine methyl ester hydrochloride in 40 ml of methylene chloride was added 4.18 g of triethylamine followed by 8.27 g of the nitrophenyl ester prepared as in Embodiment 2 above. The reaction mixture immediately became bright yellow and solids began to precipitate. The reaction mixture was stirred for 2 hours, then stored overnight at −10° C. The reaction mixture was rewarmed to room temperature, and 0.6 ml of triethylamine was added. Then, 490 mg of the D-histidine methyl ester hydrochloride was added, and stirring was continued for 2 hours. The reaction mixture was washed with 20 ml of water, then twice with 20 ml of 10% ammonium hydroxide, and then twice with 20 ml of water. All the washes were back-extracted serially with 20 ml of methylene chloride, and the combined organic phases was dried with MgSO$_4$ and stripped to 100 ml, filtered through silica, followed by 25 ml of 20% methanol in ethyl acetate. The resulting eluate was stripped to 40 ml and diluted to 120 ml with diethyl ether; the precipitated solid was filtered, washed with diethyl ether, and dried by suction to give 5.66 g of the desired product as a white solid, m.p. 114.5°–117° C. $[\alpha]_D^{20}$ −55.5 (c 2 in CHCl$_3$).

EMBODIMENT 4

CYCLO(D-PHENYLALANYL-D-HISTIDINE)

5.60 g of methyl ester of Embodiment 3 above was stirred and hydrogenated in 100 ml of methanol over 220 mg of 10% palladium on carbon at atmospheric pressure. After 3 hours, solids began to precipitate; an additional 2.5 ml of methanol was added to facilitate stirring. After 7 hours, an additional 280 ml of methanol was added as the mixture was heated to reflux. The mixture was filtered hot, and the filtrate was stripped to a gel-mush and mixed with 100 ml of diethyl ether. The resulting solid was filtered, washed with diethyl ether, and dried by suction and then under high vacuum at 35° C. to give 3.29 g of the desired product as an off-white powder, $[\alpha]_D^{23}$ = 68.5 (c 2.0 in CH$_3$COOH).

EMBODIMENT 5

S-ALPHA-CYANO-3-PHENOXYBENZYL ALCOHOL

A 100 ml three-neck Bantam ware flask was charged with 43 mg of cyclo(D-phenylalanyl-D-histidine) and put under a nitrogen atmosphere. Then, 3.51 ml of hydrogen cyanide was added by syringe causing the catalyst to swell and become a gel. After 5 minutes, 30 ml of toluene was added, causing additional catalyst to precipitate. 5.95 g of 3-phenoxybenzaldehyde was added all at once. The reaction mixture was stirred for 4.75 hours and then quenched with 20 ml of water containing 10 drops of concentrated hydrochloric acid. The toluene solution was separated, washed twice with water, and diluted to 50 ml with toluene for analysis, which showed 80% S-alpha-cyano-3-phenoxybenzyl alcohol isomer was produced.

EMBODIMENT 6

S-ALPHA-CYANO-3-PHENOXYBENZYL ALCOHOL

The reaction of Embodiment 5 above was repeated using 171 mg of cyclo(D-phenylalanyl-D-histidine). At intervals, 0.25 ml samples were removed and examined by gas liquid chromatography as follows:

| Time | % Conversion of Aldehyde |
| --- | --- |
| 35 minutes | 20 |
| 2 hours | 76 |
| 6.5 hours | 95 |

After 7 hours, the reactiom mixture was quenched by addition of 10 ml of 1 N hydrochloric acid. The organic phase was separated and washed twice with water, dried over MgSO$_4$, filtered and stored at −10° C. The filtrate was diluted to 50 ml with toluene and the optical rotation was determined to be −1.54° at 21° in 1 dm cell. A sample of the product was acetylated with p-nitro-phenylacetic anhydride and the stereoisomer ratio was determined by HPLC on a chiral Pirkle column to be 71% S-alpha-cyano-3-phenoxybenzyl alcohol and 29% R-alpha-cyano-3-phenoxybenzyl alcohol.

EMBODIMENT 7

S-ALPHA-CYANO-3-PHENOXYBENZYL ALCOHOL

Two small round-bottom flasks having magnetic stirrers and septum covers were each charged with 22.5 mg of cyclo(D-phenylalanyl-D-histidine) and put under nitrogen. A sample of 0.98 ml of hydrogen cyanide was diluted to 25 ml with toluene and 5 ml of the solution was added via syringe to each flask. After about 5 minutes, 0.87 ml of 3-phenoxybenzaldehyde (POAL) was added to each flask. Flask No. 1 was stirred in an oil bath at 35° C. and flask No. 2 was stirred in a water bath at 24°–26° C. The results of these experiments are below.

| Time, hr | Flask No. 1 | | | Flask No. 2 | | |
| --- | --- | --- | --- | --- | --- | --- |
| | POAL, % | α-Hydroxy-nitrile, % | R/S | POAL, % | α-Hydroxy-nitrile, % | R/S |
| 0.5 | 19 | 81 | 8.7/91.3 | 18 | 82 | 15.8/84.2 |
| 1 | 12 | 88 | — | 13 | 87 | 14.4/85.6 |
| 2 | 12 | 88 | — | 12 | 88 | — |
| 4 | 10 | 90 | 11.4/88.6 | 12 | 88 | 19.0/81.0 |
| 8 | 10 | 90 | — | 13 | 87 | — |

EMBODIMENT 8

S-ALPHA-CYANO-3-PHENOXYBENZYL ALCOHOL

A reaction was conducted by contacting 0.0099 m/kg cyclo-(D-phenylalanyl-D-histidine) with 0.99 m/kg of 3-phenoxybenzaldehyde followed by 2.2 m/kg of hydrogen cyanide and 190 ppm water. The reaction was conducted in toluene at 25° C. The product was obtained with 93% conversion of aldehyde and was 88% S-alpha-cyano-3-phenoxybenzyl alcohol.

EMBODIMENT 9

S-ALPHA-CYANO-3-PHENOXYBENZYL ALCOHOL

A reaction was conducted by treating 0.0200 g of cyclo(D-phenyl-alanyl-D-histidine) at 25° C. under nitrogen with 1.4037 g of 3-phenoxybenzaldehyde to disperse the catalyst followed by injecting 2.1812 g of toluene with 13.65 w % hydrogen cyanide. After 2.7 hours, 93% of the 3-phenoxybenzaldehyde was converted and the product had an S-alpha-cyano-3-phenoxybenzyl alcohol enantiomeric excess of 77%.

EMBODIMENT 10

S-ALPHA-CYANO-3-PHENOXYBENZYL ALCOHOL

A reaction was conducted at 25° C. by contacting 0.0519 g of cyclo(D-phenylalanyl-D-histidine) in 9.32 ml of diethyl ether with 1.811 g of 3-phenoxybenzaldehyde followed by 0.617 gh of hydrogen cyanide. After 3.6 hours, 99.4% of the 3-phenoxybenzaldehyde had been converted and the product had an S-alpha-cyano-3-phenoxybenzyl alcohol enantiomeric excess of 72%.

EMBODIMENT 11

A Niro Atomizer laboratory spray dryer with a ca 31 inch diameter chamber was assembled. In operation, 40 SCFM $N_2$ is heated to 140° C. and fed to the dryer chamber. A warm solution of 0.5-1.0% w cyclo(D-phenylalanyl-D-histidine) in methanol is fed via a rotary vaned atomizer to the chamber above the $N_2$ inlet. The droplets of cyclo(D-phenylalanyl-D-histidine) solution are rapidly dried to give hollow spherical particles of 1 to 10 μm diameter. The combined stream is fed to a cyclone where 50-70% of the particles are captured.

Six test runs were made using 5 to 10 gm of cyclo(D-phenylalanyl-D-histidine) each. Starting with a catalyst that was inefficient for cyanohydrination, all the products were activated to give good reaction rate and produce (S)-alpha-cyano-3-phenoxybenzyl alcohol with EE's between 75-80% at 97% conversion of 3-phenoxybenzaldehyde. Water and sodium chloride, simulating recycle operation, apparently had no effect on activation. On the other hand, the addition of urea to further disrupt crystallization of cyclo(D-phenylalanyl-D-histidine) did not result in any further improvement. The results of the six test runs are tabulated in Table 2.

TABLE 2

ACTIVATION OF CYCLO(D-PHENYLALANYL-D-HISTIDINE) FOR SPRAY DRYING

| Experiment | Catalyst Purity % w | Feed Composition (Rest MeOH) | | | | Feed Rate ml/min | $N_2$ Rate SCFM[f] | Temp In °C. | Temp Out °C. |
|---|---|---|---|---|---|---|---|---|---|
| | | DDCAT[d] % w | $H_2O$ % w | NaCl % w | Others % w | | | | |
| 1 | 87 | 0.49 | | | | 115 | 42 | 135 | 60-75 |
| 2 | 87 | 0.48 | | | | 225 | 42 | ~160 | 60-70 |
| 3 | 92[b] | 0.84 | | | | 125 | 43 | 135-140 | 55-65 |
| 4 | 92[b] | 0.63 | 4.5 | | | 110 | 43 | 139 | 65-75 |
| 5 | 92[b] | 0.62 | 4.5 | 1.0 | | 135 | 43 | 137-140 | 55-65 |
| 6 | 92[b] | 0.65 | — | — | 0.033 | 125 | 43 | 139 | 70-75 |
| 7 | 92[b] | 0.80 | — | — | — | 135 | 42 | 135-140 | 55-70 |

| Experiment | Atomizer RPM × $10^{-3}$ | Catalyst Recovery % | Particle Size μm | Cyanohydrination In Toluene at 25° C. | | |
|---|---|---|---|---|---|---|
| | | | | Time hr | POAL[e] Conversion % | (S)—POAL.CN[e] Selectivity[c] % |
| 1 | 37 | 46 | 1-12 | 1 | 92.2 | 91 |
| | | | | 2 | 95.9 | 90 |
| | | | | 4 | 96.9 | 90 |
| | | | | 5.5 | 95.9 | 90 |
| 2 | 31 | 58 | 1-12 | 1 | 91.3 | 90 |
| | | | | 3 | 95.5 | 88 |
| | | | | 4 | 96.7 | 88 |
| | | | | 5.1 | 98.4 | |
| 3 | 37 | 66[a] | 1-10 | 1 | 93 | 90 |
| | | | | 2 | 96.7 | 90 |
| | | | | 3 | 96.6 | 92 |
| | | | | 4 | 97.6 | 90 |
| 4 | 36 | 56[a] | 1-10 | 1 | 94.6 | |
| | | | | 2 | 96.9 | 90 |
| | | | | 3 | 98.7 | 89 |
| 5 | 36 | 68 | 1-10 | 1 | 93.6 | 91 |
| | | | | 2 | 96.6 | 90 |
| | | | | 3 | 95.4 | 91 |
| | | | | 4 | 97.5 | 90 |
| | | | | 5 | | 90 |
| 6 | 36 | 58 | 1-10 | 1 | 92.3 | 90 |
| | | | | 2 | 91.0 | 90 |
| | | | | 4 | 94.7 | 89 |
| | | | | 5 | 96.0 | 90 |
| 7 | 38 | 77 | 1-10 | 1 | 93.3 | 93 |
| | | | | 2 | 96.1 | 91 |
| | | | | 3 | 95.9 | 92 |
| | | | | 4 | 97.6 | 92 |

| | 5 | 96.0 | 91 |

[a]Mostly held in cyclone by static electricity.
[b]96% purity by pot. titration.
[c]EE = 2 (selectivity) - 100, %.
[d]DDCAT = cyclo(D-phenylalanyl-D-histidine)
[e]POAL = 3-phenoxybenzaldehyde, (S)—POAL.CN = (S)—α-cyano-3-phenoxybenzyl alcohol.
[f]SCFM = standard cubic feet per minute.

EMBODIMENT 12

Table 3 summarizes the results of tests and scale-up experiments to activate the cyclo(D-phenylalanyl-D-histidine) catalyst by solvent evaporation, most of which were from methanol. Whereas the catalyst recovered by conventional crystallization was not very active, rapid evaporation of methanolic solutions was rather effective in producing active catalysts (Experiments 1–11). The addition of small amounts of impurities (5–10% basis catalyst) appeared to help prevent normal crystallization (compare Experiment 1, having no impurity, to those following it in the table). Except for dimethyl sulfoxide, all of the additives gave better results than the base case. These experiments involved rapid stripping of 25 ml of methanol from 0.2 g of catalyst in a rotating evaporator. Attempts to scale up Experiment 9 were only partially successful. The product from the first experiment had an activity/enantiomeric excess of 88%/75%, as compared to 98%/88% in the smaller experiment. The second of the large experiments was even less active, 75%/47%. Longer times required to strip off large volumes of solvent resulted in greater amounts of crystallization of the dipeptide, thus resulting in a less active material. A solution to this problem is to spray dry the solution so that the solids are recovered rapidly. Solvents that may be useful in this approach are methanol, liquid ammonia, and acetic acid.

TABLE 3
ACTIVATION OF CYCLO(D-PHENYLALANYL-D-HISTIDINE) BY SOLVENT EVAPORATION

| Experiment | Method of Evaporation | Temp. °C. | Cyanohydrination[a] Conversion %/3 Hr | Enantiomeric Excess, % |
|---|---|---|---|---|
| 1 | Rapid small[b] evap. from methanol | ~0 | 83 | 79 |
| 2 | Rapid small evap. from methanol, +5% urea | ~0 | 96 | 87 |
| 3 | Rapid small evap. from methanol, +10% 3-phenoxybenzaldehyde | 0–20 | 95 | 85 |
| 4 | Rapid small evap. from methanol, +10% M acetic acid | 0–20 | 99 | 85 |
| 5 | Rapid small evap. from methanol, +10% CH₃CN | 0–20 | 99 | 86 |
| 6 | Rapid small evap. from methanol, +10% α-isopropyl-p-chlorophenyl-acetonitrile | 0–20 | 97 | 87 |
| 7 | Rapid small evap. from methanol, +7% HIS—OME/triethylamine | 0–20 | 95 | 75 |
| 8 | Rapid small evap. from methanol, +50% water | 0–20 | 92 | 80 |
| 9 | Rapid small evap. from methanol, +5% filtrate residue | 0–20 | 98 | 88 |
| 10 | Rapid small evap. from methanol, +10% dimethyl sulfoxide | 0–20 | 16 | 31 |
| 11 | Rapid small evap. from methanol, +5% Z—D-PHE—HIS—OME | 0–20 | 96 | 87 |
| 12 | Slow Evaporation from hot methanol/water | 70–90 | 67 | 63 |
| 13 | Large run similar to 9 (15 g) | | 88 | 75 |
| 14 | Large run similar to 9 (15 g) | | 75 | 47 |
| 15 | Medium run similar to 9 (7 g in 2 Hr) | | 98 | 86 |

[a]Cyanohydrination of 3-phenoxybenzaldehyde with HCN to give (S)—alpha-cyano-3-phenoxybenzyl alcohol.
[b]Small means 0.2 g of catalyst in 25 ml of solvent.

EMBODIMENT 13

Solvent precipitation is another way of activating the cyclo(D-phenylalanyl-D-histidine) dipeptide, and Table 4 summarizes some results using this approach. In all but one example shown, dimethyl sulfoxide (DMSO) was used to dissolve the catalyst as a 5% solution, and the dipeptide was precipitated by pouring this solution into a well-stirred vessel of second solvent, under a variety of conditions. In most cases, the precipitated catalyst formed a voluminous gel which was rinsed with the second solvent to remove dimethyl sulfoxide and blown dry. In Experiments 5–14 urea (5% basis catalyst) was added to the DMSO solution to aid in preventing crystallization of the dipeptide. In any case, from the results shown, it appears that (a) of the five precipitating solvents tested, dichloromethane and toluene appeared to be best; (b) high temperature (80° C.) gave better results than lower temperature (25° C.); (c) high dilution gave a better result than lower dilution (compare Experiments 5 and 6); and (d) the catalyst precipitated from liquid ammonia solution (Experiment 4) was moderately active (82% conversion in 3 hours) and quite selective (84% EE, even after 22 hours of contact with the catalyst). Unlike all of the others this product was a dense solid that was easy to filter and wash. A number of solvents for cyclo(PHE-HIS) shown in Table 1 can be used in this approach, namely, DMSO, acetic acid, formamide, 1-methyl-2-pyrrolidinone, dimethylformamide, N-methylformamide, liquid ammonia, and the like.

TABLE 4
ACTIVATION OF CYCLO(D-PHENYLALANYL-D-HISTIDINE) BY SOLVENT PRECIPITATION

| Experiment | Method of Precipitation | Cyanohydrination[d] Conversion %/3 Hr | Enantiomeric Excess, % |
|---|---|---|---|
| 1 | From dimethyl sulfoxide (5%) into diethyl ether | 65 | 41 |
| 2 | From dimethyl sulfoxide (5%) into toluene, 80° C. | 97 | 72 |
| 3 | From dimethyl sulfoxide (5%) into toluene 25° C., large scale | 74 | 37 |
| 4 | From liquid NH$_3$ (2%) into diethyl ether, −40° C. | 82 | 84[b] |
| 5 | From dimethyl sulfoxide[a] into 20V toluene, 25° C. | 42 | 31 |
| 6 | From dimethyl sulfoxide into 5V toluene, 25° C. | 4 | 10 |
| 7 | From dimethyl sulfoxide into 20V toluene, 80° C. | 85 | 57 |
| 8 | From dimethyl sulfoxide into 20V acetonitrile, 80° C./25° C. | 77 | 37[e] |
| 9 | From dimethyl sulfoxide into 20V acetonitrile, 25° C. | 2 | 18[f] |
| 10 | From dimethyl sulfoxide into 20V tetrahydrofuran, 25° C. | 2 | 19[g] |
| 11 | From dimethyl sulfoxide into 20V diethyl ether, 25° C. | 2 | 0[c] |
| 12 | From dimethyl sulfoxide into 20V dichloromethane | 77 | 49 |
| 13 | From dimethyl sulfoxide into 20V tetrahydrofuran + 1% v/v H$_2$O, 25° C. | 77 | 60 |
| 14 | Experiment 13 and vacuum oven dried | 89 | 50[h] |

[a]Catalyst 5% w/v in dimethyl sulfoxide, urea 5% basis catalyst.
[b]After 22 hours at 95% conversion.
[c]After 71 hours the enantiomeric excess was 24% at a conversion of 97%.
[d]Cyanohydrination of 3-phenoxybenzaldehyde with HCN to give (S)—alpha-cyano-3-phenoxybenzyl alcohol.
[e]At 92% conversion.
[f]At 44% conversion.
[g]At 49% conversion.
[h]After 4 hours.

EMBODIMENT 14

Another method tested for activating the catalyst is freeze drying. This approach requires a solvent for the dipeptide that freezes at a convenient temperature and is volatile enough to be sublimed at below that temperature and at a practical pressure (vacuum). Of the solvents tested, only water and acetic acid meet these requirements. The results of some of these tests are summarized in Table 5. Freeze drying of a 0.1% w solution of the dipeptide in water gave an excellent product (Experiment 5). An attempt to freeze dry a solution in dimethyl sulfoxide failed because the solvent was too high boiling to be sublimed at about 0° C. and 170 microns pressure. On the other hand, solutions in glacial acetic acid were readily freeze dried. The product from this freeze drying contains one mole of acetic acid per mole of catalyst. In spite of this, the product was surprisingly active and selective (Experiment 2). This acid is relatively loosely held by the catalyst, and it was volatilized away in a sweep of air, on the one hand (Experiment 3), or neutralized by triethylamine treatment, on the other (Experiment 4). In both cases the products had about the same activity/selectivity: 93%/72%.

TABLE 5
ACTIVATION OF CYCLO(D-PHENYLALANYL-D-HISTIDINE) BY FREEZE DRYING

| Experiment | Solvent/Work Up | Cyanohydrination[c] Conversion %/3 Hr | Enantiomeric Excess, % |
|---|---|---|---|
| 1 | From 2% solution in dimethyl sulfoxide | — | — |
| 2 | From 1.9% solution in acetic acid | 74 | 56 (6.5) |
| 3 | Product from experiment 2 air swept 2 days | 93 | 73 (5) |
| 4 | Product from Experiment 2 treated with triethylamine in diethyl ether | 93 | 72 (6.3) |
| 5 | From 0.1% solution in water | 98 | 85 (2.5) |

[a]Solution frozen at −40° C.; solvent sublimed at 0.1 Torr.
[b]Numbers in parentheses indicate time, in hours.
[c]Cyanohydrination of 3-phenoxybenzaldehyde with HCN to give (S)—alpha-cyano-3-phenoxybenzyl alcohol.

EMBODIMENT 15

S-ALPHA-CYANO-3-PHENOXYBENZYL ALCOHOL

A sample of 0.0833 g of cyclo(D-phenylalanyl-D-histidine) was activated by heating to reflux in 8 ml of methanol; the mixture was treated with periodic addition of methanol, about 11 ml total, over 1 hour until the cyclic dipeptide was dissolved. The solution was cooled in an ice bath and the methanol evaporated at a range of +6° C. and 20 mm Hg to −4° C. and 0 mm Hg. The resulting gelatinous material was heated to 50° C. to give activated cyclo(D-phenylalanyl-D-histidine).

To 0.2933 g of cyclo(D-phenylalanyl-D-histidine) in 15 ml of diethyl ether at 25° C. was added 2.907 g of 3-phenoxybenzaldehyde followed by 0.940 g of hydrogen cyanide After 2 hours, 94% of the 3-phenoxybenzaldehyde had been converted and the product had an S-alpha-cyano-3-phenoxybenzyl alcohol enantiomeric excess of 84%. After 4 to 20 hours, 99.4% of the 3-phenoxybenzaldehyde had been converted and the product had an S-alpha-cyano-3-phenoxybenzyl alcohol enantiomeric excess of 67–68%.

EMBODIMENT 16

S-ALPHA-CYANO-3-PHENOXYBENZYL S-ISOPROPYL(4-CHLOROPHENYL)ACETATE

Two 1 dram vails with toluene were each charged with 1 ml of solution containing 0.135 g of S-alpha-cyano-3-phenoxybenzyl alcohol followed by 0.504 ml of S-isopropyl(4-chlorophenyl)acetyl chloride solution in toluene.

To the first vial was added with stirring 0.07 ml of 2,6-lutidine. The resulting mixture became warm immediately and precipitated solids. Stirring was continued for 10 minutes with no further change. The mixture was washed successively with water, dilute hydrochloric acid and water, and dried (MgSO$_4$). The resulting oil contained 75.5% of the S-alpha-cyano-3-phenoxybenzyl S-isopropyl(4-chlorophenyl)acetate isomer.

To the second vial was added with stirring 0.083 ml of triethylamine. An immediate reaction occurred, and the product was recovered as described above to give an oil containing 72.0% of S-alpha-cyano-3-phenoxybenzyl S-isopropyl(4-chlorophenyl)acetate isomer.

EMBODIMENT 17

S-ALPHA-CYANO-3-PHENOXYBENZYL (1R,CIS)-2,2-DIMETHYL-3-(2,2-DICHLOROVINYL)CYCLOPROPANECARBOXYLATE

To a solution of 1 g of (1R,cis)-2,2-dimethyl-3-(2,2-dichlorovinyl)cyclopropanecarboxylic acid dissolved in 25 ml of methylene chloride was added 0.5 g of thionyl chloride followed by a few drops of dimethylformamide. The reaction mixture was refluxed overnight, and the solvent was removed under pressure at 40° C. The residue was dissolved in 20 ml benzene and 0.4 g of S-alpha-cyano-3-phenoxybenzyl alcohol (90% enantiomeric excess to S-isomer) in 2 ml of benzene was added followed by 0.5 ml of pyridine in 2 ml of benzene. The reaction mixture was stirred for 1.5 hours. The resulting solution was poured into water, extracted with ether, the ether layer was washed with dilute hydrochloric acid, then with sodium bicarbonate solution. The organic layer was washed with water, dried (MgSO$_4$) and condensed to give a yellow oil, which was chromatographed to give 0.53 g of the desired product, $[\alpha]_D^{20} = 26.55°$ (CH$_2$Cl$_2$ 0.558 g/ml).

What is claimed is:

1. A process for the preparation of an optically-active alpha-hydroxynitrile of formula I

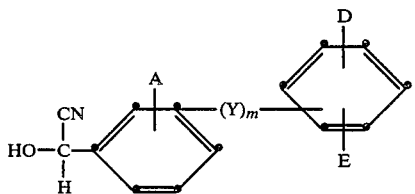

wherein m is 0 or 1; Y is O, CH$_2$, or C(O); A, D and E each independently is a hydrogen atom, a halogen atom having an atomic number of from 9 to 35, inclusive, or an alkyl or alkoxy group containing 1 to 6 carbon atoms, each optionally substituted by one or more halogen atoms having an atomic number of from 9 to 35, inclusive, or a mixture enriched therein which comprises treating the corresponding aldehyde with a source of hydrogen cyanide in the presence of a substantially water-immiscible, aprotic solvent and a cyclo(D-phenylalanyl-D-histidine) as a catalyst.

2. A process according to claim 1 wherein the solvent is an aromatic hydrocarbon, an ether or mixtures thereof.

3. A process according to claim 2 wherein the solvent is toluene, diethyl ether or a mixture of toluene and ether.

4. A process according to claim 3 wherein the solvent is diethyl ether.

5. A process according to claim 3 wherein the solvent is toluene.

6. A process according to claim 1 wherein the catalyst is well dispersed.

7. A process according to claim 3 wherein the catalyst is present in an amount of about 0.1 to about 10 mole percent based upon the weight of the aldehyde.

8. A process according to claim 5 wherein the catalyst is present in an amount of about 1.0 to about 7.5 mole percent based upon the weight of the aldehyde.

9. A process according to claim 3 wherein the aldehyde is 3-phenoxybenzaldehyde.

10. A process according to claim 1 wherein the source of hydrogen cyanide is hydrogen cyanide.

11. A process according to claim 10 wherein about 1 to about 3 moles hydrogen cyanide is used per mole of aldehyde.

12. A process according to claim 1 wherein the hydrogen cyanide is introduced concurrently with, subsequent to or rapidly followed by the solvent and/or aldehyde.

13. A process according to claim 1 wherein A, D and E each independently is a hydrogen atom, a fluorine atom, a chlorine atom, a methyl group, a trifluoromethyl group or a methoxy group.

14. A process according to claim 13 wherein D is a hydrogen atom and A and E each independently is a hydrogen atom or a fluorine atom and when either A or E is fluorine, each is located at the 4-position of the ring relative to the benzyl carbon when A or relative to the Y=O bearing carbon atom when E.

15. A process according to claim 14 wherein the alpha-hydroxynitrile is S-alpha-cyano-3-phenoxybenzyl alcohol.

16. A process according to claim 14 wherein the alpha-hydroxynitrile is S-alpha-cyano-4-fluoro-3-phenoxybenzyl alcohol or S-alpha-cyano-3-(4-fluorophenoxy)benzyl alcohol.

* * * * *